United States Patent [19]
Schlumberger

[11] Patent Number: 5,356,034
[45] Date of Patent: Oct. 18, 1994

[54] APPARATUS FOR THE PROPORTIONED FEEDING OF AN ANALYSIS FLUID

[75] Inventor: Helmut Schlumberger, Polling, Fed. Rep. of Germany

[73] Assignee: Boehringer Mannheim GmbH, Mannheim, Fed. Rep. of Germany

[21] Appl. No.: 8,552

[22] Filed: Jan. 22, 1993

[30] Foreign Application Priority Data

Jan. 30, 1992 [DE] Fed. Rep. of Germany ....... 4202561

[51] Int. Cl.⁵ ................................................. B67D 5/08
[52] U.S. Cl. ...................................... 222/61; 222/399; 222/462; 222/504; 222/559
[58] Field of Search ................. 222/61, 386, 394, 399, 222/401, 460, 462, 504, 559; 251/129.06, 129.17

[56] References Cited

U.S. PATENT DOCUMENTS

| | | | |
|---|---|---|---|
| 3,762,605 | 10/1973 | Seaton | 222/504 X |
| 4,142,656 | 3/1979 | Smith et al. | 222/325 |
| 4,177,926 | 12/1979 | Hunter | 239/99 |
| 4,203,554 | 5/1980 | Zimmer et al. | 239/585 |
| 4,629,099 | 12/1986 | Jones | 222/504 X |
| 4,714,234 | 12/1987 | Falk et al. | 251/129.17 |
| 4,762,277 | 8/1988 | Pater et al. | 239/99 |
| 4,877,745 | 10/1989 | Hayes et al. | 436/166 |
| 4,928,111 | 5/1990 | Walton | 346/1.1 |
| 4,962,871 | 10/1990 | Reeves | 222/504 |
| 5,065,910 | 11/1991 | Fiedler | 222/504 |

FOREIGN PATENT DOCUMENTS

| | | |
|---|---|---|
| 0119573 | 9/1984 | European Pat. Off. . |
| 0165407 | 12/1985 | European Pat. Off. ....... 251/129.06 |
| 0260929 | 3/1988 | European Pat. Off. . |
| 0276053 | 7/1988 | European Pat. Off. . |
| 3302617 | 8/1984 | Fed. Rep. of Germany . |
| 0288782 | 12/1987 | Japan ............................ 251/129.06 |
| WO 86/05722 | 10/1986 | PCT Int'l Appl. . |
| 1055267 | 1/1967 | United Kingdom . |

OTHER PUBLICATIONS

Patent Abstract of SU-1366-226-A; Auga, 1988 Derwent Publications Ltd.

Primary Examiner—Andres Kashnikow
Assistant Examiner—Joseph A. Kaufman
Attorney, Agent, or Firm—Nikaido, Marmelstein, Murray & Oram

[57] ABSTRACT

Apparatus for proportioned feeding of an analysis fluid (7) onto a target (5), ejects fluid onto the target in small quantities pulse-wise out of a nozzle (2) through a nozzle outlet opening (3). The apparatus allows the precise proportioning of analysis fluid quanta which are substantially larger than in the case of the "drop on demand" methods commonly used to date for analysis fluids, but are smaller than the minimum doses achievable to date with diluters and dispensers. The apparatus includes a pressure chamber (1) in which the analysis fluid is held under pressure, and a valve unit (11) with a valve opening. A closing element is moved by a positioning element. The valve unit (11) is constructed so that the ejection of the fluid is supported by the movement of the closing element (13) during the closure of the valve opening (23).

24 Claims, 3 Drawing Sheets

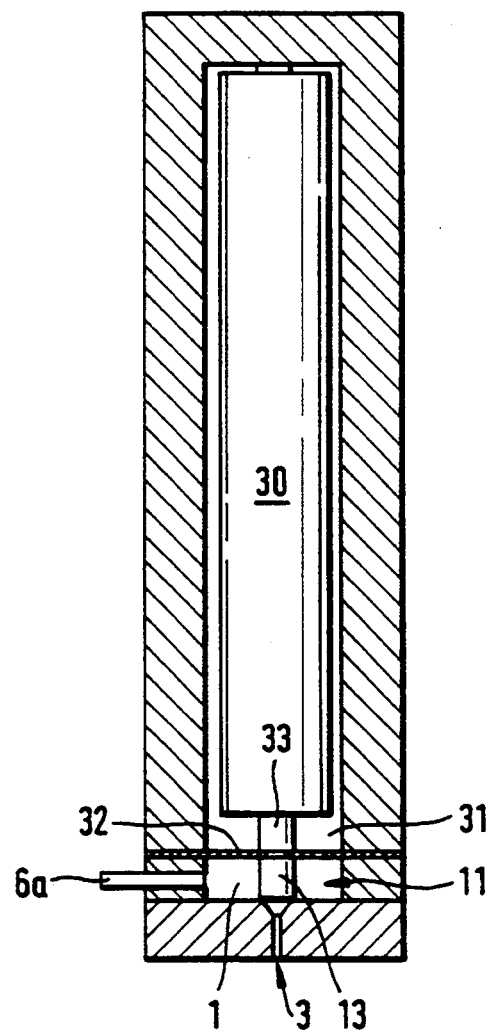
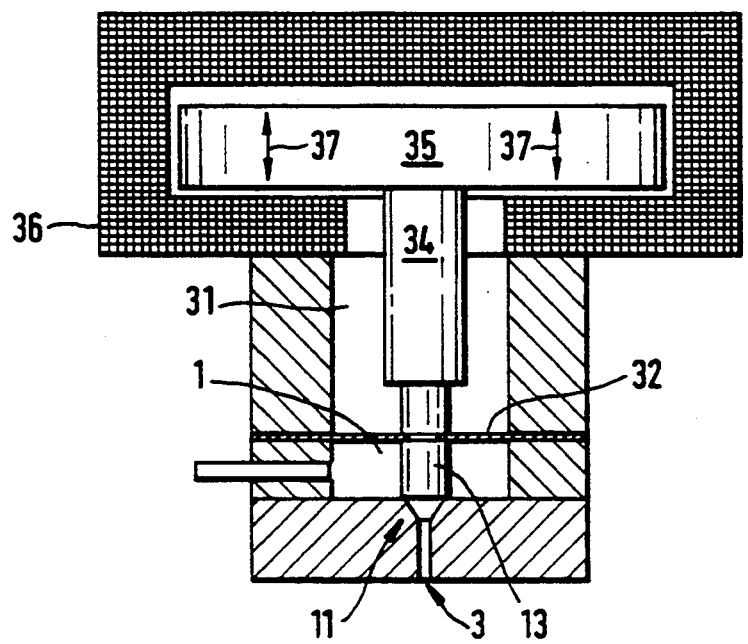

APPARATUS FOR THE PROPORTIONED FEEDING OF AN ANALYSIS FLUID

BACKGROUND OF THE INVENTION

1. Field of the Invention

The invention relates to an apparatus for the proportioned feeding of an analysis fluid onto a target, in which the fluid is ejected onto the target in small quanta pulse-wise out of a nozzle through a nozzle outlet opening.

In clinical chemistry it is often necessary to apply an analysis fluid onto a target in exact quantity. The fluid may be for example a reagent fluid, a calibration fluid or a sample fluid, in particular blood or serum.

The target to which the fluid is to be fed may be a reaction vessel, for example in an automatic analysis unit. Other examples are the microtitre plates frequently used in microbiology and the solid phase analysis elements in very common use today, which are also described as "test carriers" and, in the Anglo-Saxon literature, as "solid state analysis elements". For the purpose of the present invention the term "analysis elements" denotes in addition to discrete test carriers (such as e.g. test strips and analysis slides) also tapes, strips or other forms of continuous analysis elements which are directed past a proportioning station at which the analysis fluid is applied.

2. Description of the Prior Art

Use is traditionally made for the feeding of analysis fluids of various forms of piston-cylinder apparatuses, such as e.g. pipettes, dispensers and diluters. The reagents have usually been applied to analysis elements by impregnation of the reagents-carrier matrix (for example paper) or a reagent film has been produced in a layer-forming process from a fluid containing film-forming polymers. Printing techniques have also been proposed.

In EP-A-119 573 and in EP-A-268 237 (U.S. Pat. No. 4,877,745) apparatuses of the kind mentioned in the preamble are described. Their technique is based on the ink jet technology developed originally for computer printers (ink jet printers). Both documents contain more detailed explanations of the known state of the art, to which reference is made here.

These known apparatuses for the microproportioning of analysis fluids have in each case a nozzle compartment whose volume is compressed for a short time in order to eject a quantum of analysis fluid. In the case of EP-A-119 573 the nozzle compartment is formed by a section of an elastic tube, against whose lateral surface an electromagnetically moved cylindrical rod is directed, which is moved against the tube whenever a drop is to be ejected. In the case of EP-A-268 237 the nozzle compartment consists of a tubular piece which is surrounded by a coaxial piezoelectric actuating element likewise formed in a tubular shape.

The "drop on demand" printing techniques make it possible to apply extremely small volumes of analysis fluids contact-free, accurately and quickly onto a target. The extraordinarily small volume of the individual quanta, which is usually some 0.2 nl and does not exceed about 1 nl, is however disadvantageous for many applications. If larger volumes are required, hundreds or thousands of jet quanta have to be ejected one after the other. The time required is considerable despite the high injection rate. In the case of easily volatile reagent fluids there is the risk that a substantial proportion of the small droplets will evaporate. In addition the ejection of the quanta is interrupted if a gas bubble of minute size forms in the nozzle compartment in the vicinity of the nozzle outlet opening. In the case of printers the formation of such gas bubbles can be avoided by the use of special inks. In the case of analysis fluids, however, this solution is not an option.

SUMMARY OF THE INVENTION

The aim of the invention is to provide an apparatus for the proportioned feeding of an analysis fluid onto a target, which avoids the aforementioned disadvantages and makes possible to generate analysis fluid quanta of precisely determined volume which are substantially larger than in the case of the "drop on demand" methods commonly used to date for analysis fluids, but on the other hand are smaller than the minimum doses achievable to date with diluters and dispensers.

The aim is achieved in the case of an apparatus of the kind mentioned in the preamble by the fact that the latter comprises a pressure chamber in which the analysis fluid is held under pressure, a valve unit with a valve opening in the flow path of the fluid from the pressure chamber to the nozzle outlet opening and with a closing element moved by a positioning member for the opening and closing of the valve opening is provided, and the valve unit is constructed so that the ejection of the fluid is supported by the movement of the closing element on the closure of the valve opening.

In the case of the present invention, in contrast to the apparatuses for "drop on demand" microproportioning described above, a nozzle compartment (which is located directly behind the nozzle outlet opening) is not compressed whenever a fluid quantum is to be ejected. Instead, the nozzle outlet opening is hydraulically connected to a pressure chamber in which the analysis fluid is subjected to a permanent pressure (of for example 0.1 to 5 bar). The ejection of a quantum of analysis fluid is controlled by the closing element of the valve unit, which briefly opens the hydraulic connection between the pressure chamber and the nozzle outlet opening and closes again.

Said technique is known for the application of markings to packages and other comparatively rough and ready printing jobs. In particular there is supplied by the firm Domino Printing Sciences under the name "Makrojet 2" a device which ejects fluid quanta of some 1.7 $\mu$l. The closing element of the valve unit is pressed by a spring against the nozzle outlet opening and for opening it is retracted with an electromagnetic tie rod (solenoid) by means of a wire pull. Details of said technique are given in DE-A-33 02 617, EP-A-0 260 929 and (in another embodiment) EP-A-0 276 053.

The known apparatus is however completely unsuitable for the microproportioning of analysis fluids, because in said field (in contrast to the printing of comparatively rough and ready markings) a very high accuracy of the proportioning is required, which cannot be achieved with the known apparatus. The variation coefficient (VC) of the drop size of the Makrojet 2 is above 10%, whereas for analysis purposes a maximum VC of around 1% is aimed at. Moreover, in the case of the known apparatus the lower limit of the achievable volume of a quantum is relatively high.

In the context of the present invention it has been found that it is highly advantageous for the high precision of the proportioning required during the proportioning of analysis fluids if the valve unit is deliberately so constructed that the ejection of the fluid during the closure operation, i.e. by the movement of the closing element in the direction of the closed state (closed position) of the valve unit, is not arrested, but supported and promoted.

BRIEF DESCRIPTION OF THE DRAWINGS

The invention will be explained in detail below with reference to an exemplifying embodiment shown in the figures, where.

DESCRIPTION OF THE PREFERRED EMBODIMENTS

Figure 1:
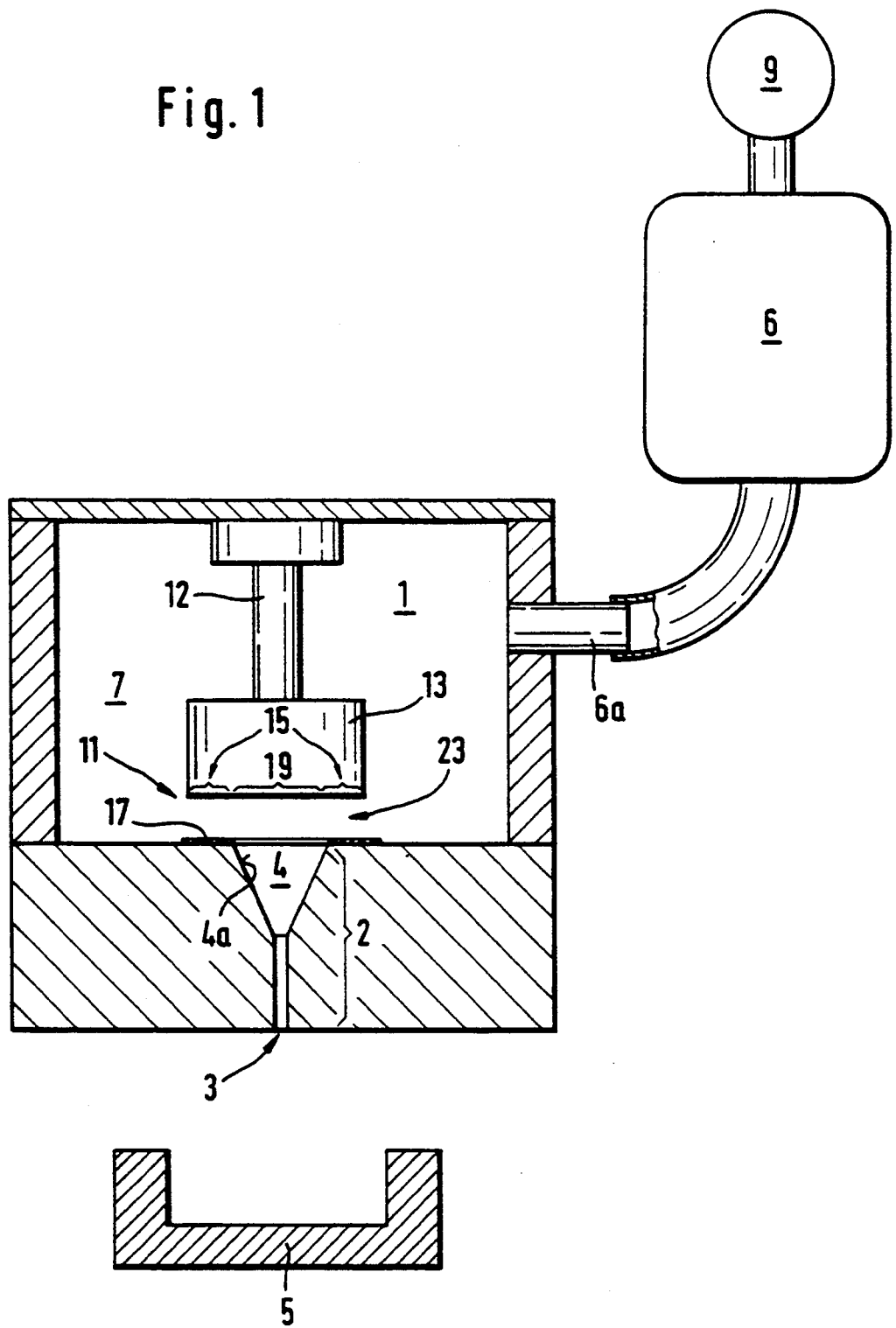
FIG. 1 shows the overall layout of an apparatus according to the invention in cross-section, FIG. 2 an embodiment of the invention with a piezoelectric positioning element in cross-section, FIG. 3 an embodiment of the invention with a magnetic positioning element in cross-section, FIG. 4 a detailed view of a preferred valve unit.

The apparatus shown in FIG. 1 for the microproportioning of analysis fluids comprises a pressure chamber 1 for the analysis fluid and a nozzle 2 with a nozzle outlet opening 3 and a nozzle pre-chamber 4, through which the analysis fluid may be ejected in small quanta onto a target 5 (shown simply schematically). The analysis fluid 7 is held under pressure in the pressure chamber 1. It is fed by means of a pressure generating device 9 out of a storage vessel 6 via a connecting branch 6a. A pump, for example, may serve as the pressure generating device 9. It is also possible however for the pressure of an external pressure source (for example compressed air) to be transmitted via a diaphragm onto the analysis fluid 7 in the pressure chamber 1.

The hydraulic connection between the pressure chamber 1 and the nozzle outlet opening 3 may be opened and closed by means of a valve unit 11. The valve unit 11 (which is shown with the valve in the open position in FIG. 1 and is also referred to below simply as a valve) comprises a closing element 13 actuated by a positioning member 12, the annular sealing rim 15 of said closing element 13 pressing with the valve unit 11 in the closed position against a likewise annular sealing seat 17 in the manner of a disc seal. The area surrounded by the sealing rim 15 is designated as the closing area 19.

Positioned in front of the sealing seat 17 in the direction of the nozzle outlet opening 3 is the nozzle pre-chamber 4, which with the exception of the valve outlet opening and (with the valve opened) of the valve opening 23 is closed.

For the functioning according to the invention the hydraulic conditions in the region of the valve 11 and the nozzle 2 are of particular importance. In this respect the following features are preferred.

The closing area 19 is greater than the nozzle outlet opening 3. This causes a "hydraulic gearing up" or "hydraulic transmission" during the closure of the closing element 13, i.e. the fluid moves during the closure of the closing element 13 considerably faster through the nozzle outlet opening 3 than the closing element 13 moves in the direction of the nozzle outlet opening 3. The ejection of the fluid is thereby supported and promoted particularly well during the closure of the valve 11 with a relatively slow movement of the closing element 13.

Particular importance attaches %o the hydraulic gearing up in the context of the invention. In order to ensure the required ejection of the fluid in the ink jet technology (the so-called "jetting"), the flow rate in the nozzle should be at least 1 m/s. in the context of the invention it has been found that during the closing of the valve also a similarly high rate is required in order to achieve a precise interruption of the fluid flow. Without the hydraulic gearing up it is therefore essential that the closing element moves at a rate of the order of magnitude of 1 m/s from the open position into the closed position. The difficulties associated with said high rate (damage to the sealing seat of the valve, damage to the positioning member, rebound of the closing element out of the closed position) are avoided by means of the hydraulic gearing up. Optimum flow kinetic conditions may be achieved with reasonable structural outlay.

The walls 4a of the nozzle pre-chamber 4 are from the sealing seat 17 to the nozzle outlet opening 3 preferably cone-shaped at least in certain sections. In order to ensure the hydraulic gearing up, the closing element should moreover not be provided with a congruent cone, instead it is preferable for the closing area 19 to be roughly level (as shown), curved slightly inwards or, if it is curved in the direction of the nozzle outlet opening 3, at least significantly flatter than the conical walls 4a of the nozzle pre-chamber 4. Although a conical seal with mutually engaging congruent sealing surfaces will be regarded as advantageous for the sealing in many cases, it is nevertheless disadvantageous in the context of the invention because of the desired hydraulic gearing up.

For the effectiveness of the hydraulic gearing up it is advantageous if the opening cross-section of the valve opening 23 of the valve 11, which is formed by the annular gap between the sealing rim 15 and the sealing seat 17, is smaller than the closing area 19. On the other hand the opening cross-section of the valve opening 23 should be greater than the cross-section of the nozzle outlet opening 3. It is thereby ensured that with the valve opened the flow rate of the analysis fluid is determined in the main by the flow resistance of the outlet opening 3 and not by the flow resistance of the valve.

The precision in volume terms of the ejected fluid quanta is improved by all these measures.

In the case of the embodiment shown in FIG. 2 the closing element 13 is actuated by means of a piezoelectric positioning element 30. It is shown with the valve 11 in the closed position. In order to bring about the required positioning path, a stacking piezo for example may be used.

The piezoelectric positioning element 30 is located in a positioning member compartment 31 which is separated from the pressure chamber 1 by a diaphragm 32. The diaphragm 32 blocks off completely the pressure chamber 1 from the positioning member compartment 31. The closing element 13 is rigidly connected to the positioning member 30, the connecting element penetrating the diaphragm 32. The diaphragm is provided with a sealing border at the penetration point.

In the context of the present invention it has been found that such a diaphragm seal is particularly advantageous for ensuring an exact proportioning. In general the seal between the pressure chamber 1 and the adjacent positioning member compartment 31 should be frictionless, so that the moving of the closing element 13 by the positioning element 30 is not arrested by frictional forces.

The piezoelectric valve movement permits a rapid sequence of movements with high forces. In addition it makes it possible for the closing element 13 to be brought deliberately and relatively exactly into a desired position between the closed position and the open position. This is particularly advantageous in connection with the embodiment explained with reference to FIG. 4.

FIG. 3 shows an embodiment in which the closing element 13 is actuated by a magnetic positioning member 34. It comprises a swinging armature 35 which may be moved to and fro in the direction of the arrows 37 by a magnetic coil 36 as a function of the polarity of the current flow. Magnetic actuation makes possible sufficiently high actuating frequencies, and simultaneously a relatively long actuating path (of the order of magnitude of 1 mm). It is of particular advantage in the context of the invention that the positioning movement does not slow down towards the ends of the positioning path, but is even accelerated. The direct magnetic actuation of the closing element therefore makes it possible for the closing movement to adopt a course which is particularly favourable for the invention. The closing element 13 is thereby during the closure of the valve 11 moved at an undiminished or even increasing speed in the direction of the nozzle outlet opening 3 until the sealing rim (not shown in FIG. 3) abuts against the sealing seat. In this exemplifying embodiment also a diaphragm 32 is provided in order to separate the pressure chamber 1 from the positioning member compartment 31.

Figure 4:
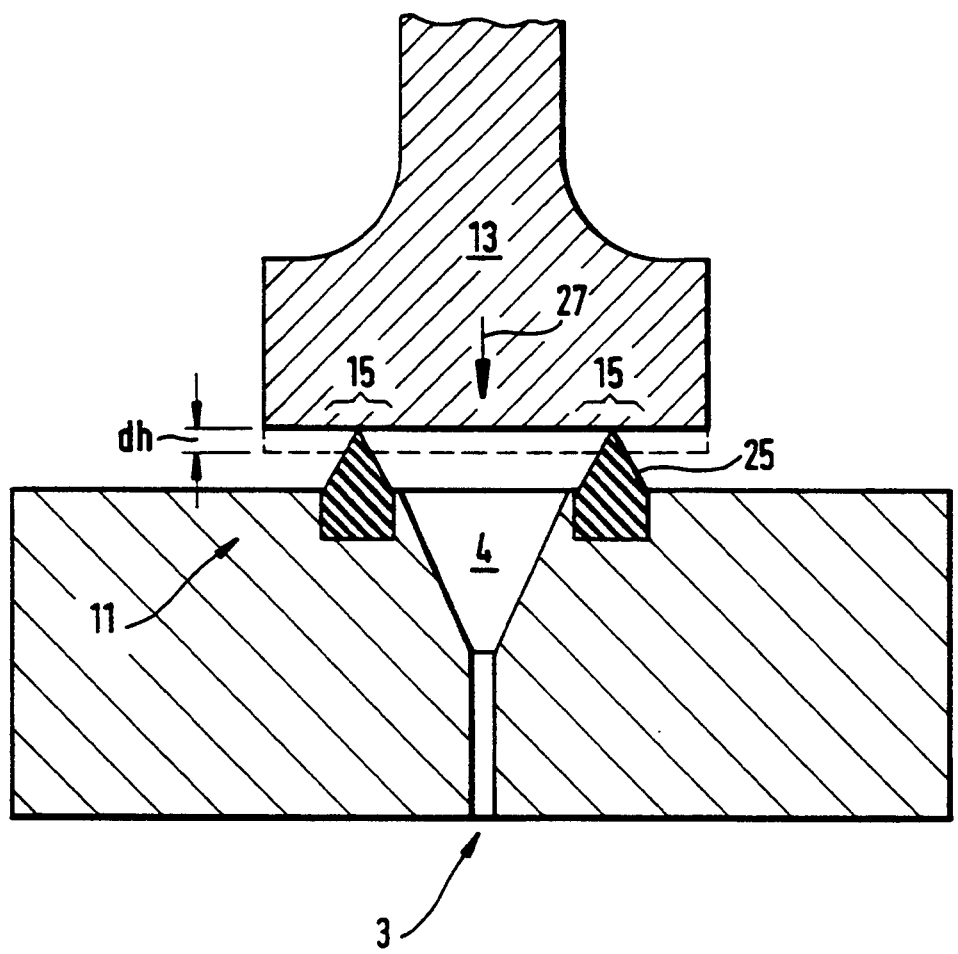

FIG. 4 illustrates a further preferred embodiment, in which the sealing element of the valve 11 exhibits elasticity such that the closing element 13 is movable beyond a position which ensures the hydraulic seal in the direction of the nozzle outlet opening 3. In the embodiment shown the sealing seat 17 comprises for this purpose an elastic seal 25, for example in the form of a shaped packing ring, against which the sealing rim 15 of the closing element 13 presses. The hydraulic seal is moreover already ensured the moment that the sealing rim 15 contacts the elastic seal 25. Said position of the sealing element 13 is shown in continuous lines. If the latter, due to the pressure of the closing element 13 in the direction of the nozzle outlet opening 3 (arrow 27), is further compressed by the positioning path difference dh (said position is shown in dashes in the figure), the complete sealing ("chamber effect") of the fluid enclosed in the nozzle pre-chamber 4 leads to a particularly rapid ejection of the fluid at the moment of the closing of the valve 11.

On the opening of the valve 11 the "chamber effect" results in a small volume of air being sucked in through the nozzle outlet opening 3. This is not disadvantageous for the precision of the volumetric proportioning if the volume sucked in is relatively small.

Because of the elasticity of the seal 25 the closing element will after the attainment of the foremost position be pressed back slightly in the direction of the nozzle compartment if the positioning member permits such a movement. Consequently a drop of fluid remaining at the nozzle outlet opening 3 after the ejection of the fluid quantum will be drawn back. The precision in volume terms of the ejected fluid quanta will also be increased as a result. A concave inwardly curved meniscus is obtained in the region of the nozzle outlet opening 3.

I claim:

1. An analysis fluid microproportioning apparatus for microproportioned feeding of an analysis fluid onto a target, comprising:
    a pressure chamber for holding the analysis fluid under a permanent pressure of at least 0.1 bar;
    a valve unit having a valve opening disposed in a flow path of the fluid between the pressure chamber and a nozzle, said valve unit having a closing element which is moved by a positioning member for opening and closing the valve opening, said permanent pressure forcing fluid through said valve opening when said valve opening is open, wherein the valve unit controls ejection of the fluid onto a target in small quantities in a pulse-wise manner, and wherein the fluid ejection is supported by movement of the closing element when the closing element is moved toward a closing position of the valve unit,
    wherein the closing element of the valve unit comprises a closing face facing an input side of the nozzle, said closing face being defined by a sealing rim, said sealing rim being disposed opposite an annular sealing seat disposed adjacent said input side of the nozzle, wherein the nozzle comprises a nozzle pre-chamber disposed toward said input side of the nozzle, said nozzle pre-chamber being closed on an input side thereof when said valve unit is in a closed position by said sealing rim tightly fitting against said annular sealing seat, and wherein a surface formed by said closing face and said sealing rim facing the nozzle does not substantially protrude into said nozzle pre-chamber.

2. An apparatus according to claim 1, wherein walls of the nozzle pre-chamber from the input side thereof toward the nozzle outlet opening are at least partly cone-shaped.

3. An apparatus according to claim 1, wherein a cross-section of the valve opening in the open position of said closing element is greater than a cross-section of the nozzle outlet opening.

4. An apparatus according to claim 1, wherein the valve unit further comprises an elastic sealing means disposed between the closing face and an input side of the nozzle, said elastic sealing means being compressible beyond an initial contact position with said closing element and said input side of the nozzle for creating a hydraulic seal an ejecting an amount of analysis fluid through the nozzle during a compression of the elastic sealing means.

5. An apparatus according to claim 1, wherein the closing element of the valve unit is actuated by a piezoelectric positioning member.

6. An apparatus according to claim 1, wherein the closing element of the valve unit is actuated by an electromagnetic positioning member.

7. An apparatus according to claim 1, wherein the pressure chamber is sealed off from the positioning member by a sealing means.

8. An apparatus as recited in claim 7, wherein said sealing means sealingly separates the pressure chamber from the positioning member without affecting the movement of the positioning member.

9. An apparatus according to claim 8, wherein the sealing means comprises a diaphragm.

10. An apparatus as recited in claim 1, wherein a maximum diameter of said sealing rim is greater than a maximum diameter of said nozzle pre-chamber.

11. An apparatus according to claim 1, wherein a maximum diameter of the input side of the nozzle pre-chamber is larger than a maximum diameter of an output side of said nozzle pre-chamber.

12. An apparatus as recited in claim 1, wherein a cross-section of the valve opening in the open position of said closing element is smaller than a surface area of the closing face, said cross-section of the valve opening in the open position extending between said sealing rim and said sealing seat.

13. An apparatus according to claim 1, wherein said nozzle means includes a pre-chamber portion toward an input side thereof, with an output side of the pre-chamber portion having a larger cross-section area than an output side thereof.

14. An apparatus according to claim 13, wherein walls of the nozzle pre-chamber from the input side thereof toward the nozzle outlet opening are at least partly cone-shaped.

15. An analysis fluid microproportioning apparatus for microproportioned feeding of an analysis fluid onto a target, comprising:
a pressure chamber for holding the analysis fluid under a permanent pressure of at least 0.1 bar;
a valve unit having a valve opening disposed in a flow path of the fluid between the pressure chamber and a nozzle, said valve unit having a closing element which is moved by a positioning member for opening and closing the valve opening, said permanent pressure forcing fluid through said valve opening when said valve opening is open, wherein the valve unit control ejection of the fluid onto a target in small quantities in a pulse-wise manner, and wherein the fluid ejection is supported by movement of the closing element when the closing element is moved toward a closing position of the valve unit,
wherein the closing element of the valve unit comprises a closing face facing an input side of the nozzle, said closing face being defined by a sealing rim, said sealing rim being disposed opposite an annular sealing seat disposed adjacent said input side of the nozzle, wherein the nozzle comprises a nozzle pre-chamber disposed toward said input side of the nozzle, said nozzle pre-chamber being closed on an input side thereof when said valve unit is in a closed position by said sealing rim tightly fitting against said annular sealing seat, and wherein a surface area of the closing face of the closing elements is greater than a cross-section of a nozzle outlet opening, and wherein a speed of a closing movement of the closing element and a ratio of the cross-section of the closing face to the cross-section of the nozzle outlet opening are configured such that a flow rate of the analysis liquid through the nozzle remains essentially unchanged throughout the closing movement.

16. An apparatus according to claim 15, wherein said nozzle means includes a pre-chamber portion toward an input side thereof, with an input side of said pre-chamber portion having a larger cross-section area than an output side thereof.

17. An apparatus according to claim 16, wherein walls of the nozzle pre-chamber from the input side thereof toward the nozzle outlet opening are at least partly cone-shaped.

18. An apparatus according to claim 15, wherein said ejection means further comprises elastic sealing means disposed between the closing means and the nozzle means, said elastic sealing means being compressible beyond an initial contact position with said closing means and said input side of the nozzle, for creating a hydraulic seal and ejecting an amount of analysis fluid through the nozzle means during a compression of the elastic sealing means.

19. An apparatus according to claim 15, wherein said pressure chamber means is sealed off from said positioning means by a sealing means.

20. An apparatus according to claim 19, wherein said sealing means comprises a diaphragm.

21. An apparatus according to claim 15, wherein a cross-section of the valve opening in the open position of said closing element is greater than a cross-section of the nozzle outlet opening.

22. An apparatus according to claim 15, wherein the closing element of the valve unit is actuated by a piezoelectric positioning member.

23. An apparatus according to claim 15, wherein the closing element of the valve unit is actuated by an electromagnetic positioning member.

24. An apparatus as recited in claim 15, wherein a cross-section of the valve opening in the open position of said closing element is smaller than a surface area of the closing face, said cross-section of the valve opening in the open position extending between said sealing rim and said sealing seat.

* * * * *